(12) United States Patent
Wang et al.

(10) Patent No.: US 11,214,778 B2
(45) Date of Patent: Jan. 4, 2022

(54) PREPARATION OF LIPASE WITH IMPROVED ESTER SYNTHESIS ACTIVITY BY USING SURFACTANTS

(71) Applicant: Jiangnan University, Wuxi (CN)

(72) Inventors: Dong Wang, Wuxi (CN); Yan Xu, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/034,325

(22) Filed: Sep. 28, 2020

(65) Prior Publication Data

US 2021/0017505 A1 Jan. 21, 2021

Related U.S. Application Data

(63) Continuation of application No. 16/284,511, filed on Feb. 25, 2019, now abandoned, which is a continuation of application No. PCT/CN2017/117787, filed on Dec. 21, 2017.

(30) Foreign Application Priority Data

Jun. 8, 2017 (CN) .......................... 201710425990.7

(51) Int. Cl.
*C12N 9/20* (2006.01)
*C12N 9/96* (2006.01)

(52) U.S. Cl.
CPC .................. *C12N 9/20* (2013.01); *C12N 9/96* (2013.01); *C12Y 301/01003* (2013.01)

(58) Field of Classification Search
None
See application file for complete search history.

(56) References Cited

PUBLICATIONS

S.Y. Huang et al. "Preparation of surfactant-coated lipase for the esterification of geraniol and acetic acid in organic solvents", Enzyme and Microbial Technology 22:552-557 (Year: 1998).*
R.K. Owusu et al. "Interfacial parameters for selected Spans and Tweens at the hydrocarbon-water interface", Food Hydrocolloids 10(1):27-30. (Year: 1996).*

* cited by examiner

*Primary Examiner* — Richard G Hutson
(74) *Attorney, Agent, or Firm* — IPro, PLLC; Na Xu

(57) ABSTRACT

The present disclosure discloses a method for preparing lipase with high ester synthesis activity by using surfactant, belonging to the field of enzyme engineering. The present disclosure provides a method for obtaining a lipase with high ester synthesis activity by adding different surfactants with different concentrations in a lipase aqueous solution and then freeze-drying. The lipase meets the requirement in non-aqueous catalysis. Mixing a variety of lipase with no ester synthesis activity or low activity at suitable concentration and an appropriate concentration of the surfactant in the solution can produces lipases with significantly improved ester synthesis activity, meanwhile changing the hydrolytic activity of the lipase. Increased ester synthesis activity makes lipase more suitable for industrial applications.

6 Claims, No Drawings

PREPARATION OF LIPASE WITH IMPROVED ESTER SYNTHESIS ACTIVITY BY USING SURFACTANTS

TECHNICAL FIELD

The disclosure herein relates to the preparation of lipase with improved ester synthesis activity by using surfactants, which belongs to the field of enzyme engineering.

BACKGROUND

Lipase (triacylglycerol ester hydrolases, EC 3.1.1.3), firstly reported in 1901, is a class of biocatalysts hydrolyzing long-chain triacylglycerol ester at the water-oil interface and widely exists in animals, plants and microorganisms. Besides the hydrolysis of ester bonds, lipases can catalyze esterification and transesterification reaction in non aqueous environments and therefore gain great interest in the field of biological chemical industry. As being able to facilitate very special chemical transformation, lipases are gaining more and more interest in several industries such as food, detergents, cosmetics, organic synthesis, pharmaceutical. For example, they can be used in progressing food, wastewater treatment, synthesis of biological surfactants, treatment of wood cellulose pulp paper resin and biosynthesis of chiral drugs. Lipases also have advantages of good stability and high conversion efficiency and they have application value in the production of aromatic esters, biodiesel and chiral compounds.

Most lipases can catalyze hydrolysis of ester bonds. However, only few catalyzes ester synthesis reaction in non-aqueous media and most microbial lipases do not display apparent activity when catalyzing ester synthesis reaction in non-aqueous media. Several heterologous expressed lipases display only remarkable hydrolysis activity but little ability to catalyze synthesis of esters in comparison with wild-type lipases. The industrial application of lipases is hampered by their poor activities catalyzing ester synthesis reaction.

Several protein-modified methods, such as enzyme immobilization and pretreatment with organic solvent, have been adapted to adjust or improve activity of enzyme. But these methods cannot change catalytic performance of lipases essentially. Besides, surfactants can adjust catalytic performance and generally improve the lipase activity of hydrolysis. Employing surfactants to enhance lipase activity in non-aqueous media have also been reported decades ago, including formation of surfactant-coated enzyme or reverse micelle system, both of which will improve the solubility of enzymes in non-aqueous media, and molecular bio-imprinting technologies—lyophilize lipases in the presence of surfactants and wash them off afterwards. Although sometimes effective, these methods are complicated and time-consuming in practice and cannot be applicable to all the lipases. Developing a straightforward, versatile method to improve the activity of lipase catalyzing ester synthesis in non-aqueous has a significant practical value.

SUMMARY

To solve the problems above, the present disclosure provides a method for preparation of the lipases meeting the requirement of practical application in non-aqueous catalysis, which have high ester synthesis activity, by changing microstructures of lipases via the interaction between surfactants and soluble lipases in aqueous environments and lyophilizing mixture afterwards. The present disclosure also provides a method which can be applicable to other lipases.

The present disclosure provides a method for enhancing ester synthesis activity of lipases by using surfactants. The present disclosure relates to modify lipases by adding surfactants and obtain lipases by lyophilization, which are able to catalyze synthesis of esters. The present disclosure solves the problem that many recombinant lipases do not display ester synthesis activity, and lays the foundation for expanding the industrial application of lipase. The present disclosure is obviously different from the existing methods for modifying lipase by using surfactants to obtain high ester synthesis activity, and has good operability and wide applicability.

The method for enhancing ester synthesis activity of lipases is to directly add surfactants to the lipase solution and mix afterwards, which can provide a hydrophobic environment enabling soluble lipases to regain the ester synthesis activity by changing the microstructure of lipases.

In an embodiment of the present disclosure, the ester synthesis activity described refers to the activity of catalyzing synthesis of esters in a non-aqueous phase.

In an embodiment of the present disclosure, the aqueous solution of the lipase described refers to the solution obtained by dissolving the lipase (powder) directly in an aqueous solution.

In an embodiment of the present disclosure, the aqueous solution described can be water and other buffer solutions.

In an embodiment of the present disclosure, the buffer solution can be phosphate buffer, citrate buffer, acetate buffer, Tris buffer and the like.

In an embodiment of the present disclosure, the concentration of buffer solution ranges from 25 to 100 mmol·L$^{-1}$ pH 6.5-8.0.

In an embodiment of the present disclosure, the buffer is a 25 mmol·L$^{-1}$ phosphate buffer pH 7.5.

In an embodiment of the disclosure, the lipases described include, but are not limited to, *Rhizopus chinensis* lipase r27RCL, *Rhizoupus oryzae* lipase ROL, *Pseudomonas cepacia* lipase PCL, *Candida antarctica* lipase CALB, and the like.

In an embodiment of the disclosure, the lipase can be a lipase that is heterologously expressed, a lipase expressed by a recombinant microorganism, or any other lipases that have lower or no ester synthesis activity relative to the wild-type lipase.

In an embodiment of the present disclosure, the protein concentration of the pure enzyme in the soluble lipase solution described ranges from 0.1 and 0.4 mg·mL$^{-1}$ to ensure that lipases interact with surfactants completely.

In an embodiment of the present disclosure, the surfactant described can be one or a combination of a zwitterionic surfactant, a nonionic surfactant, a cationic surfactant, and the like. Different surfactants have different effects on different lipases. But surfactants described are not limited to the above-mentioned surfactants.

In an embodiment of the present disclosure, the zwitterionic surfactants are 3-[(3-Cholamidopropyl)dimethylammonio]-1-propanesulfonate (CHAPS), polyethylene glycol octylphenyl Ether (Triton X-100), 1-myristyl 2-acyl-cis-propyltri-phosphatidylcholine (LPC14), 1,2-dihexanoyl lecithin (DiC6PC), 1-(LPC16), 1-Lauramate-2-acyl-cis-propyltri-phosphatidylcholine (LPC16), 1-myristyl-2-acyl-cis (LPG12), 1-caramom-2-acyl-cis-propyltriyl-phosphoric acid-1-glycerol(LPG14), 1-palm-2-acyl-cis (LPG16), 1,2-diheptanoyl-S-glycero-3-phosphorylcholine (DHPC), or a combination of two or more.

In an embodiment of the present disclosure, the nonionic surfactants described are n-dodecyl-β-D-maltopyranoside (DDM), octaethylene glycol monododecyl ether (C12E8), n-decyl-β-D-maltopyranoside (DM), n-undecyl-β-D-maltopyranoside (UDM), n-octyl-β-D-glucopyranoside (OG), octaethylene glycol monodecyl ether (C10E8), or a combination of two or more.

In an embodiment of the present disclosure, the cationic surfactants described are hexadecyl trimethyl ammonium bromide (CTAB) and the like.

In an embodiment of the present disclosure, the surfactant aqueous solution can be stored at 4° C. for a short time.

In an embodiment of the present disclosure, the protein solution and the surfactant solution are mixed at a volume ratio ranging from 1:0.5 to 1:2.

In an embodiment of the present disclosure, the protein solution and the surfactant solution are mixed at a volume ratio of 1:1.

In an embodiment of the present disclosure, the final concentration of the surfactant ranges from 0.1 times the critical micelle concentration (0.1×CMC) to 200 times the critical micelle concentration (200×CMC).

In an embodiment of the present disclosure, the final concentration of the surfactant ranges from 10 times the critical micelle concentration (10×CMC) and 200 times the critical micelle concentration (200×CMC).

In an embodiment of the present disclosure, the final concentration of the surfactant is 100 times the critical micelle concentration (100×CMC).

In an embodiment of the present disclosure, the amount of surfactant added is high enough to make the final concentration range from 1 to 500 mM.

In an embodiment of the present disclosure, the amount of surfactant added is high enough to make the final concentration reach 10 mM.

In an embodiment of the present disclosure, the addition of surfactants can further enhance ester synthesis activity and/or total recovery of ester synthesis activity of *Rhizopus chinensis* lipase r27RCL, *Rhizoupus oryzae* lipase ROL, *Pseudomonas cepacia* lipase PCL, *Candida antarctica* lipase CALB and the like.

In an embodiment of the present disclosure, the method comprises the step of removing the water after mixing.

The second object of the present disclosure is to provide a lipase preparation with improved activity catalyzing ester synthesis in a non-aqueous phase, wherein the lipase preparation is prepared by dissolving a lipase in an aqueous solution, directly adding a surfactant, mixing, and then removing the water.

In an embodiment of the present disclosure, the step of removing the water described can be the drying, and lyophilizaton.

In an embodiment of the present disclosure, the aqueous solution described can be water and other buffer solutions.

In an embodiment of the disclosure, the lipases described can be a lipase that is heterologously expressed, a lipase expressed by a recombinant microorganism, or any other lipases that have lower or no ester synthesis activity relative to the wild-type lipase.

The third object of the present disclosure is to provide the application of the lipase described in ester synthesis reaction.

In an embodiment of the present disclosure, the ester synthesis reaction is a ester synthesis reaction in non-aqueous phase.

The fourth object of the present disclosure is to provide the application of lipases described in the field of food, chemical, biological, pharmaceutical, environmental, and petroleum.

In an embodiment of the present disclosure, the application includes, but is not limited to, detergents production, cosmetics production, wastewater treatment, bio-surfactants production, wood cellulose pulp paper resins treatment, biosynthesis of chiral drugs, aromatic ester production, biodiesel production, chiral compound production and the like.

Beneficial effect of the present disclosure:

(1) Conformation and function of protein are closely related to the environments around. The present disclosure provides a method of producing lipases with high ester synthesis activity by in vitro adjustment of lipase activity by simulating cellular membrane hydrophobic environment using surfactants.

(2) The method of the present disclosure is applicable to *Rhizopus chinensis* lipase r27RCL expressed by *Pichia pastoris*, commercial *Rhizoupus oryzae* lipase ROL, commercial *Pseudomonas cepacia* lipase PCL, commercial *Candida antarctica* lipase CALB and the like. The method described can help lipase regain ester synthesis activity or increase ester synthesis activity by 8-30 times, and enable the total recovery of lipase ester synthesis activity reach 105%-1733%.

DETAILED DESCRIPTION

Determination of Lipase Activity (1) Determination of hydrolytic activity of the lipase using p-nitrophenyl palmitate (pNPP) as substrate Hydrolysis of pNPP catalyzed by lipase generates p-nitrophenol and palmitic acid. p-nitrophenol appears yellow in the buffer at pH 8.0 with the maximum absorption peak at 410 nm. Determination of hydrolytic activity can be achieved by measuring the absorbance at 410 nm.

The substrate solution A: 50 mmol·L$^{-1}$ sodium phosphate buffer (pH 8.0) containing 1.16 g·L$^{-1}$ sodium deoxycholate and 0.56 g·L$^{-1}$ arabic gum. Substrate solution B: 0.015 g pNPP is dissolved in 5 mL isopropyl alcohol. Substrate solution A and substrate solution B are mixed then stored for use afterwards.

Termination solution: 40 g·L$^{-1}$ NaOH, 93.05 g·L$^{-1}$ EDTA sodium. Add 62 uL termination solution to the reaction mixture when stopping the reaction.

Determination method:

Add 0.1 mL appropriately diluted enzyme solution, which is substituted by inactivated enzyme solution as the control, to 2.4 mL substrate solution above, incubate the mixture at 40° C. for 2 min and measure the absorbance at 410 nm.

Definition of enzyme activity:

one hydrolytic activity unit is defined as the amount of enzyme that catalyzes the formation of 1 μmol of p-nitrophenol in 1 minute at 40° C.

Calculation equation:

enzyme activity (U·mL$^{-1}$)=(V×A$_{410}$×10$^{6}$)/(ε×t×V')

where V is the volume of the reaction mixture (mL), ε is the molar extinction coefficient (mL·mmol$^{-1}$), t is the reaction time (min) and V' is the volume of the enzyme solution (mL).

(2) Determination of ester synthesis activity of the lipase by GC analysis

Reaction substrates:

Substrate solution A: 48.5 mL of n-octanoic acid is dissolved in 250 mL of n-heptane in a volumetric flask.

Substrate solution B: 17.5 mL of absolute ethanol is dissolved in 250 mL of n-heptane in a volumetric flask.

Internal standard: 2-hexanol/n-heptane (35 g·L$^{-1}$).

Standard sample: 10 g of n-octanoate is dissolved in 1000 mL of n-heptane in a volumetric flask.

Method of Determination 1 mL substrate solution A and substrate solution B are added in a 5 mL Eppendorf tube respectively, then 20 mg lipase powder (or lyophilized powder) is added. The reaction is carried out at 40° C. and with shaking at 150 rpm for 30 min. Remove the lipase powder by centrifugation or membrane filtration. Then 0.1 mL of internal standard is added in 0.4 mL of filtrate or supernatant and mixed. Measure the content of n-octanoate in the mixture above by GC analysis.

The gas chromatograph (6820, Agilent Instruments) is equipped with a AC20 (PEG20000)capillary column and a FID detector. Nitrogen was used as the carrier gas. The oven temperature was programmed to start at 90° C. for 1 min and then be elevated to 200° C. for 5 min at 10° C.·min$^{-1}$. The injector and detector temperatures were set at 250° C.

Definition of enzyme activity: One unit of ester synthesis activity is defined as the amount of enzyme that esterifies 1 micromole of n-octanoate per min.

Calculation equation:

$$\text{enzyme activity } (U \cdot mg^{-1}) = \frac{A_{sam}}{A_{sta}} \times S_{sta} \times V \times 10^6 \times \frac{1}{172} \times \frac{1}{30} \times \frac{1}{m}$$

$A_{sam}$—the ratio of the peak areas of the sample for testing to the internal standard;

$A_{sta}$—the ratio of the peak areas of the standard sample to the internal standard;

$S_{sta}$—the concentration of the standard sample (g~L$^{-1}$);

V—the volume of the reaction mixture (L);

m—the amount of lipase in the reaction mixture (mg).

Specific activity: the activity of lipase per milligram of Natalprotein in the lipase preparation.

Total recovery: the percentage of the activity after a treatment to that before the treatment

EXAMPLE 1

Method of Operation for Enhancing Lipase Ester Synthesis Activity

Add an equal volume of high-concentration surfactant solution into the enzyme solution. The final protein concentration was 0.25 mg·mL$^{-1}$ and the surfactant concentration was 10 mM. After mixed thoroughly, the mixture was lyophilized and kept in dry condition.

EXAMPLE 2

Regain of the Ester Synthesis Activity of Commercial r27RCL

Commercial lipase r27RCL was purchased from Jiangsu Yiming Biological Technology Co., Ltd, which has high hydrolytic activity and low ester synthesis activity. Dissolve the r27RCL powder in water and centrifuge to obtain the supernatant containing the r27RCL lipase to adjust the ester synthesis activity (the final protein concentration was 0.2 mg·mL$^{-1}$ and the final concentration of surfactant was 10 mM, which is between 0.1×CMC~200×CMC of the different surfactants in Table 1). As shown in Table 1, addition of LPC14 increased the ester synthesis specific activity from 5.5 U·mg$^{-1}$ to 47.6 U·mg$^{-1}$ and the total recovery of ester synthesis activity was 769% while the hydrolytic specific activity did not show significant change.

TABLE 1

Ester synthesis activity and hydrolytic activity of r27RCL.

|  | surfactant | Specific activity (U · mg$^{-1}$) | Total recovery (%) |
|---|---|---|---|
| Ester synthesis activity | blank | 5.5 | 100 |
|  | CTAB | 0 | 0 |
|  | DiC6PC | 15.9 | 256 |
|  | C12E8 | 22.2 | 372 |
|  | LPC14 | 47.6 | 769 |
|  | DDM | 31.4 | 423 |
|  | CHAPS | 13.0 | 105 |
|  | Triton X-100 | 12.9 | 192 |
| Hydrolytic activity | blank | 115.7 | 100 |
|  | CTAB | 0 | 0 |
|  | DiC6PC | 104.2 | 87 |
|  | C12E8 | 117.1 | 101 |
|  | LPC14 | 116.1 | 97 |
|  | DDM | 135.0 | 94 |
|  | CHAPS | 132.6 | 109 |
|  | Triton X-100 | 116.6 | 93 |

EXAMPLE 3

Regain of the Ester Synthesis Activity of Commercial ROL

Commercial lipase ROL was purchased from Sigma-Aldrich Co., Ltd. ROL is a non-immobilized lipase. Dissolve the ROL powder in water and centrifuge to obtain the supernatant containing the ROL lipase that would be regulated to improve its ester synthesis activity by adjusting the final protein concentration to 0.2 mg·mL$^{-1}$ and adding surfactants to the final concentration of 10 mM. As shown in Table 2, addition of LPC14 increased its ester synthesis specific activity from 0.4 U·mg$^{-1}$ to 12.2 U·mg$^{-1}$ and the total recovery of ester synthesis activity was 1733%.

TABLE 2

Ester synthesis activity and hydrolytic activity of ROL.

|  | surfactant | Specific activity (U · mg$^{-1}$) | Total recovery (%) |
|---|---|---|---|
| Eester synthesis activity | blank | 0.4 | 100 |
|  | CTAB | 0 | 0 |
|  | DiC6PC | 3.11 | 733 |
|  | C12E8 | 2.6 | 400 |
|  | LPC14 | 12.2 | 1733 |
|  | DDM | 2.8 | 333 |
|  | CHAPS | 2.6 | 400 |
|  | Triton X-100 | 1.7 | 200 |
| Hydrolytic activity | blank | 18.5 | 100 |
|  | CTAB | 0 | 0 |
|  | DiC6PC | 15.2 | 76 |
|  | C12E8 | 23.7 | 82 |
|  | LPC14 | 33.1 | 106 |
|  | DDM | 42.7 | 116 |
|  | CHAPS | 23.6 | 81 |
|  | Triton X-100 | 34.9 | 99 |

EXAMPLE 4

Regain of the Ester Synthesis Activity of Commercial PCL

Commercial lipase PCL was purchased from Sigma-Aldrich Co., Ltd. PCL is a non-immobilized lipase. Dissolve the PCL powder in water and centrifuge to obtain the supernatant containing the PCL lipase that would be regulated to improve the ester synthesis activity by adjusting the final protein concentration to 0.2 mg·mL$^{-1}$ and adding surfactants to the final concentration of 10 mM. As shown in Table 3, addition of DDM increased its ester synthesis specific activity from 2.5 U·mg$^{-1}$ to 55.6 U·mg$^{-1}$ and the total recovery of ester synthesis activity was 1435%.

TABLE 3

Ester synthesis activity and hydrolytic activity of PCL.

| | surfactant | Specific activity (U · mg$^{-1}$) | Total recovery (%) |
|---|---|---|---|
| Ester synthesis activity | Blank | 2.5 | 100 |
| | CTAB | 0 | 0 |
| | DiC6PC | 7.1 | 260 |
| | C12E8 | 4.6 | 130 |
| | LPC14 | 44.6 | 1260 |
| | DDM | 55.6 | 1435 |
| | CHAPS | 4.7 | 130 |
| | Triton X-100 | 6.3 | 174 |
| Hydrolytic activity | blank | 214.8 | 100 |
| | CTAB | 75.5 | 29 |
| | DiC6PC | 308.2 | 140 |
| | C12E8 | 281.1 | 98 |
| | LPC14 | 321.8 | 119 |
| | DDM | 327.7 | 111 |
| | CHAPS | 248.0 | 101 |
| | Triton X-100 | 364.5 | 131 |

EXAMPLE 5

Increase of the Ester Synthesis Activity of Commercial CALB

Commercial lipase CALB was purchased from Sigma-Aldrich Co., Ltd. CALB is a non-immobilized lipase. Dissolve the CALB powder in water and centrifuge to obtain the supernatant containing the CALB lipase that would be regulated to improve the ester synthesis activity by adjusting the final protein concentration to 0.12 mg·L$^{-1}$ and adding surfactants to the final concentration of 10 mM. As shown in Table 4, addition of DDM increased the ester synthesis specific activity from 7.8 U·mg$^{-1}$ to 101.9 U·mg$^{-1}$ and the total recovery of ester synthesis activity was 700%.

TABLE 4

Ester synthesis activity and hydrolytic activity of CALB.

| | surfactant | Specific activity (U · mg$^{-1}$) | Total recovery (%) |
|---|---|---|---|
| Ester synthesis activity | Blank | 7.8 | 100 |
| | CTAB | 36.6 | 300 |
| | DiC6PC | 31.9 | 400 |
| | C12E8 | 62.8 | 467 |
| | LPC14 | 36.8 | 411 |
| | DDM | 101.9 | 700 |
| | CHAPS | 5.9 | 44 |
| | Triton X-100 | 77.4 | 544 |

TABLE 4-continued

Ester synthesis activity and hydrolytic activity of CALB.

| | surfactant | Specific activity (U · mg$^{-1}$) | Total recovery (%) |
|---|---|---|---|
| Hydrolytic activity | blank | 1.1 | 100 |
| | CTAB | 0 | 0 |
| | DiC6PC | 0.98 | 85 |
| | C12E8 | 0 | 0 |
| | LPC14 | 0.54 | 38 |
| | DDM | 0 | 0 |
| | CHAPS | 1.6 | 92 |
| | Triton X-100 | 0 | 0 |

EXAMPLE 6

Effect of Concentration of Surfactant LPC14 on Ester Synthesis Activity of Commercial r27RCL Commercial lipase r27RCL was purchased from Jiangsu Yiming Biological Technology Co., Ltd. r27RCL is a lipase with high hydrolytic activity but low ester synthesis activity. Dissolve the r27RCL powder in water, centrifuge to obtain the supernatant and treat the supernatant with different concentrations of surfactant LPC14 (the final protein concentration was 0.2 mg·mL$^{-1}$). As shown in Table 5, ester synthesis activity of r27RCL obtained more improvement at higher concentration of surfactant LPC14 (100×CMC).

TABLE 5

Effect of concentration of LPC14 on ester synthesis activity and hydrolytic activity of r27RCL.

| | concentration (x CMC) | Specific activity (U · mg$^{-1}$) | Total recovery (%) |
|---|---|---|---|
| Ester synthesis activity | 0 | 5.5 | 100 |
| | 0.1 | 1.8 | 32 |
| | 1 | 1.4 | 25 |
| | 100 | 17.1 | 292 |
| Hydrolytic activity | 0 | 115.7 | 100 |
| | 0.1 | 120.2 | 101 |
| | 1 | 122.2 | 102 |
| | 10 | 128.0 | 107 |
| | 100 | 125.7 | 102 |

EXAMPLE 7

Effect of Concentration of Surfactant LPC14 on Ester Synthesis Activity of Commercial ROL Commercial lipase ROL was purchased from Sigma-Aldrich Co., Ltd. and is a non-immobilized lipase. Dissolve the ROL powder in water, centrifuge to obtain the supernatant and treat the supernatant with different concentrations of surfactant LPC14 (the final protein concentration was 0.2 mg·mL$^{-1}$). As shown in Table 6, ester synthesis activity obtained more improvement at higher concentration of surfactant LPC14 (10×100×CMC).

TABLE 6

Effect of concentration of LPC14 on ester synthesis activity and hydrolytic activity of ROL.

| | concentration (x CMC) | Specific activity (U · mg$^{-1}$) | Total recovery (%) |
|---|---|---|---|
| Ester synthesis activity | 0 | 0.4 | 100 |
| | 0.1 | 0.4 | 97 |
| | 1 | 0.2 | 46 |
| | 10 | 1.0 | 240 |
| | 100 | 6.2 | 1517 |
| Hydrolytic activity | 0 | 18.5 | 100 |
| | 0.1 | 28.7 | 150 |
| | 1 | 27.7 | 139 |
| | 10 | 31.2 | 162 |
| | 100 | 39.0 | 206 |

EXAMPLE 8

Effect of Concentration of Surfactant DDM on Ester Synthesis Activity of Commercial PCL Commercial lipase PCL was purchased from Sigma-Aldrich Co., Ltd. and is a non-immobilized lipase. Dissolve the PCL powder in water, centrifuge to obtain the supernatant and treat the supernatant with different concentrations of surfactant DDM (the final protein concentration was 0.2 mg·mL$^{-1}$). As shown in Table 7, ester synthesis activity obtained more improvement at higher concentration of surfactant DDM (10×-100×CMC).

TABLE 7

Effect of concentration of DDM on ester synthesis activity and hydrolytic activity of PCL

| | concentration (x CMC) | Specific activity (U · mg$^{-1}$) | Total recovery (%) |
|---|---|---|---|
| Ester synthesis activity | 0 | 2.5 | 100 |
| | 0.1 | 3.2 | 58 |
| | 1 | 2.9 | 57 |
| | 10 | 20.0 | 260 |
| | 100 | 101.6 | 2776 |
| Hydrolytic activity | 0 | 214.8 | 100 |
| | 0.1 | 499.5 | 106 |
| | 1 | 434.7 | 99 |
| | 10 | 756.7 | 114 |
| | 100 | 773.5 | 246 |

EXAMPLE 9

Effect of Concentration of Surfactant DDM on Ester Synthesis Activity of Commercial CALB Commercial lipase CALB was purchased from Sigma-Aldrich Co., Ltd. and is a non-immobilized lipase. Dissolve the CALB powder in water, centrifuge to obtain the supernatant and treat the supernatant with different concentrations of surfactant DDM (the final protein concentration was 0.12 mg·mL$^{-1}$). As shown in Table 8, ester synthesis activity obtained more improvement at higher concentration of surfactant DDM (100×CMC).

TABLE 8

Effect of concentration of DDM on ester synthesis activity and hydrolytic activity of CALB.

| | concentration (x CMC) | Specific activity (U · mg$^{-1}$) | Total recovery (%) |
|---|---|---|---|
| Ester synthesis activity | 0 | 7.8 | 100 |
| | 0.1 | 4.0 | 12 |
| | 1 | 14.3 | 50 |
| | 10 | 37.3 | 73 |
| | 100 | 32.6 | 189 |
| Hydrolytic activity | 0 | 1.1 | 100 |
| | 0.1 | 2.1 | 45 |
| | 1 | 3.0 | 75 |
| | 10 | 0.7 | 10 |
| | 100 | 0 | 0 |

In summary, the present disclosure obtains the lipase preparation with high ester synthesis activity by in vitro regulating the activity of the lipase by simulating the hydrophobic microenvironment around the protein using surfactants. The ester synthesis activity of the lipase r27RCL expressed by *Pichia pastoris* was increased from 5.5 U·mg$^{-1}$ to 47.6 U·mg$^{-1}$ and the total ester synthesis activity recovery was 769% after the surfactant treatment. The ester synthesis activity of commercial ROL was increased from 0.4 U·mg$^{-1}$ to 12.2 U·mg$^-$, and the total activity recovery was 1733% after the surfactant treatment. The ester synthesis activity of commercial PCL was increased from 2.5 U·mg$^-$ to 55.6 U·mg$^{-1}$, and the total activity recovery was 1435% after the surfactant treatment. The ester synthesis activity of commercial CALB was increased from 7.8 U·mg$^{-1}$ to 101.9 U·mg$^{-1}$, and the total activity recovery was 700% after the surfactant treatment. The concentrations of surfactant used significantly affected the regain of lipase ester synthesis activity. The higher concentration (10×100×CMC) of the surfactant can result in better lipase ester synthesis activity. The increase of both the specific activity and total activity recovery indicated that the activity regulation by simulating the hydrophobic environment of cell membrane in vitro had a positive effect on the ester synthesis activity of lipase. This method was not only applicable to r27RCL, but also to other lipases.

The disclosure described and claimed herein is not to be limited in scope by the specific aspects herein disclosed. Any person skilled in the art can make modifications without departing from the spirit and scope of the disclosure. The scope of protection of the present disclosure should therefore be defined by the claims.

What is claimed is:

1. A method for increasing ester synthesis activity of lipase, comprising:
    adding surfactant directly to an aqueous solution of soluble lipase, and mixing,
    wherein the soluble lipase comprises *Rhizopus chinesis* lipase r27RCL,
    wherein the surfactant comprises n-dodecyl-β-D-maltopyranoside, and
    wherein the surfactant is present at a final concentration of from 1 mM to 500 mM and from 0.1 times to 200 times critical micelle concentration.

2. The method for increasing the ester synthesis activity of lipase according to claim 1, comprising dissolving the lipase in powder form directly into the aqueous solution.

3. The method for increasing the ester synthesis activity of lipase according to claim 1, wherein the aqueous solution comprises phosphate buffered saline or Tris-HCl buffer.

4. The method for increasing the ester synthesis activity of lipase according to claim 1, wherein the soluble lipase is heterologously expressed by a recombinant microorganism.

5. The method for increasing the ester synthesis activity of lipase according to claim 1, wherein protein concentration of lipase in the aqueous solution of the soluble lipase is between 0.1 mg/mL and 0.4 mg/mL.

6. A lipase preparation obtained by:
dissolving the lipase in an aqueous solution;
adding surfactant directly to the aqueous solution;
wherein the soluble lipase comprises *Rhizopus chinesis* lipase r27RCL,
wherein the surfactant comprises n-dodecyl-β-D-maltopyranoside, and
wherein the surfactant is present at a final concentration of from 1 mM to 500 mM and from 0.1 times to 200 times critical micelle concentration; and
removing water from the aqueous solution.

\* \* \* \* \*